(12) United States Patent
Nebolsin et al.

(10) Patent No.: US 8,912,185 B2
(45) Date of Patent: Dec. 16, 2014

(54) USE OF GLUTARIC ACID DERIVATIVES OR THE PHARMACEUTICALLY ACCEPTABLE SALTS THEREOF AS ANTI-ARRHYTHMIC AGENTS

(71) Applicant: Obschestvo S Ogranichennoi Otvetstvennostyu "Pharmenterprises", Moscow (RU)

(72) Inventors: Vladimir Evgenievich Nebolsin, Moscow (RU); Dmitry Sergeevich Blinov, Saransk (RU); Vladimir Pavlovich Balashov, Saransk (RU); Tatyana Alexandrovna Kromova, Kaluga (RU); Galina Alexandrovna Zheltukhina, Moscow (RU)

(73) Assignee: Obschestvo S Ogranichennoi Otvetstvennostyu "Pharmenterprises", Moscow (RU)

( * ) Notice: Subject to any disclaimer, the term of this patent is extended or adjusted under 35 U.S.C. 154(b) by 0 days.

(21) Appl. No.: 13/961,019

(22) Filed: Aug. 7, 2013

(65) Prior Publication Data
US 2013/0324540 A1 Dec. 5, 2013

Related U.S. Application Data

(62) Division of application No. 12/922,958, filed as application No. PCT/RU2009/000133 on Mar. 18, 2009, now abandoned.

(30) Foreign Application Priority Data

Mar. 19, 2008 (RU) .................... 2008110644

(51) Int. Cl.
*A61K 31/535* (2006.01)
*C07D 207/09* (2006.01)
*C07D 295/13* (2006.01)
*C07D 209/20* (2006.01)
*A61K 31/4172* (2006.01)
*C07D 333/20* (2006.01)
*A61K 31/405* (2006.01)
*C07D 233/64* (2006.01)
*C07D 213/40* (2006.01)

(52) U.S. Cl.
CPC ............ *C07D 295/13* (2013.01); *C07D 207/09* (2013.01); *C07D 209/20* (2013.01); *A61K 31/4172* (2013.01); *C07D 333/20* (2013.01); *A61K 31/405* (2013.01); *C07D 233/64* (2013.01); *C07D 213/40* (2013.01)
USPC ....................................... 514/237.8

(58) Field of Classification Search
None
See application file for complete search history.

(56) References Cited

U.S. PATENT DOCUMENTS

2005/0180953 A1  8/2005  Nebolsin et al. ............. 424/85.4

FOREIGN PATENT DOCUMENTS

WO   99/01103      1/1999
WO   2006/135280  12/2006

OTHER PUBLICATIONS

Moore E N and Spear J P "Acute Animal Models for the Study of Antiarrhythmic Drugs for the Prevention of Sudden Coronary Death," Clin. Pharmacol. Antiarrhythmic Therapy, New York, 1984, pp. 31-46.

*Primary Examiner* — Craig Ricci
(74) *Attorney, Agent, or Firm* — Dilworth & Barrese, LLP

(57) ABSTRACT

The invention relates to the use of glutaric acid derivatives of general formula (I), which are disclosed in the invention description, as anti-arrhythmic agents.

1 Claim, No Drawings

USE OF GLUTARIC ACID DERIVATIVES OR THE PHARMACEUTICALLY ACCEPTABLE SALTS THEREOF AS ANTI-ARRHYTHMIC AGENTS

The instant invention relates to medicine and to the use of glutaric acid derivatives, in particular N-acyl amino acid derivatives and pharmaceutically acceptable salts thereof as anti-arrhythmic agents for correction of disorders in the rhythm of cardiac activity.

BACKGROUND ART

It is well-known that at the present time propranolol (anaprilin, obzidan) and amiodaron (cordaron) are anti-arrhythmic agents that are widely used in clinical practice.

Their main defects are insufficient effectiveness and low therapeutic diapason, which is manifested by the high frequency of cardial and extracardial side effects. [Mashkovsky M. D. Medicaments. Manual for doctors. Publication 15. Publishing House Novaya Volna. 2005. pages 390-392, 264-266].

The analog of the claimed compounds that is closest in respect to action is the N-succinyl-D,L-tryptophane dipotassium salt exhibiting anti-ischemic, cardiotonic and anti-arrhythmic action upon research [Bulletin of experimental biology and medicine. 1998. vol. 125. No. 5. pages 544-547].

A defect of the known compound is the low anti-arrhythmic activity upon parenteral administration, and also insufficient diapason of therapeutic action.

In view of the aforesaid, what is real is the search for new anti-arrhythmic agents that are capable of manifesting high anti-arrhythmic activity upon parenteral administration and are highly effective upon treatment of disorders of cardiac rhythm.

The anti-allergic and hypolipidemic action of N-acyl derivatives of biogenic amines, for example, glutaryl histamine, is described in the publication of international application WO 99/01103.

Histidine and tryptophane N-acyl derivatives of amino acids are disclosed in the publication of international application WO 2006/135280, wherein the use thereof as anti-allergic and lipid-controlling agents is described.

A description is provided in the publication of application RU 2005118635 of N-acyl derivatives of amino acids, which derivatives have anti-allergic, anti-inflammatory and hypolipidemic action and may be used for the treatment of allergic diseases: bronchial asthma, allergic rhinitis, pollinosis, seasonal rhinitis, year-round rhinitis, atopic dermatitis, psoriasis, hives, allergic (including anaphylactic) reactions to insect bites and drugs, cold allergy, allergic conjunctivitis, chronic obstructive pulmonary diseases, in particular chronic obstructive bronchitis, emphysema, obliterating bronchitis, mucoviscidosis, and also diseases related to disorders of lipid exchange, such as atherosclerosis, obesity, cardial and cerebral ischemia, cardiac infarction, stroke.

It was found by the authors of the instant invention that some of the amino acid N-acyl derivatives have anti-arrhythmic action and may be effectively used in the therapy of cardiac rhythm disorders.

The object of the instant invention is to use glutaric acid derivatives and the pharmaceutically acceptable salts thereof as anti-arrhythmic agents.

BRIEF DESCRIPTION OF THE INVENTION

The instant invention relates to the use of glutaric acid derivatives of general formula (I):

$$HOOC-(CH_2)_3-CO-NH-CH(CH_2R_1)-R_2 \quad (I)$$

wherein $R_1$ = imidazolyl, indolyl, 5-hydroxyindolyl, 5-methoxyindolyl, 5-benzyloxyindolyl, pyridyl, N-methylimidazolyl, morpholinyl, pyridyl, pyrrolyl, piperidinyl, pyrrolidinyl, N-methylpyrrolidinyl, thienyl, N-methylimidazolyl;

$R_2$ = COOH, —COOCH$_3$, —COOC$_2$H$_5$, H, or pharmaceutically acceptable salts thereof as anti-arrhythmic agents.

Further, the instant invention relates to a pharmaceutical composition and to an agent having anti-arrhythmic action, comprising an effective amount of a compound of formula (I) or a pharmaceutically acceptable salt thereof and also, if necessary, a pharmaceutically acceptable carrier.

One more subject matter of the invention is a method of treating arrhythmia, comprising administering an effective amount of a compound of formula (I) or a pharmaceutically acceptable salt thereof.

DETAILED DESCRIPTION OF THE INVENTION

The compounds of general formula (I) are presented in Table I.

TABLE I

| Compound | No. compound | $R_1$ | $R_2$ |
|---|---|---|---|
| HOOC—(CH$_2$)$_3$—CO—NH—CH(COOH)—CH$_2$-(indol-3-yl) | II | indol-3-yl | —COOH |

TABLE I-continued

| Compound | No. compound | R₁ | R₂ |
|---|---|---|---|
| HOOC—(CH₂)₃—CO—NH—CH(COOH)—CH₂—[imidazole] | III | [imidazole] | —COOH |
| HOOC—(CH₂)₃—CO—NH—CH₂—CH₂—[imidazole] | IV | [imidazole] | H |
| HOOC—(CH₂)₃—CO—NH—CH(COOC₂H₅)—CH₂—[indole] | V | [indole] | —COOC₂H₅ |
| HOOC—(CH₂)₃—CO—NH—CH(COOC₂H₅)—CH₂—[imidazole] | VI | [imidazole] | —COOC₂H₅ |
| HOOC—(CH₂)₃—CO—NH—CH(COOCH₃)—CH₂—[imidazole] | VII | [imidazole] | —COOCH₃ |
| HOOC—(CH₂)₃—CO—NH—CH(COOCH₃)—CH₂—[indole] | VIII | [indole] | —COOCH₃ |
| HOOC—(CH₂)₃—CO—NH—CH₂—CH₂—[4-pyridyl] | IX | [4-pyridyl] | H |
| HOOC—(CH₂)₃—CO—NH—CH₂—CH₂—[2-pyridyl] | X | [2-pyridyl] | H |
| HOOC—(CH₂)₃—CO—NH—CH₂—CH₂—[5-methoxyindole] | XI | [5-methoxyindole] | H |
| HOOC—(CH₂)₃—CO—NH—CH₂—CH₂—[N-methylimidazole] | XII | [N-methylimidazole] | H |
| HOOC—(CH₂)₃—CO—NH—CH₂—CH₂—[indole] | XIII | [indole] | H |

TABLE I-continued

| Compound | No. compound | R₁ | R₂ |
|---|---|---|---|
| HOOC—(CH₂)₃—CO—NH—CH₂—CH₂-(5-benzyloxyindol-3-yl) | XIV | 5-benzyloxyindol-3-ylmethyl | H |
| HOOC—(CH₂)₃—CO—NH—CH₂—CH₂-(5-hydroxyindol-3-yl) | XV | 5-hydroxyindol-3-ylmethyl | H |
| HOOC—(CH₂)₃—CO—NH—CH₂—CH₂—N(morpholino) | XVI | morpholinomethyl | H |
| HOOC—(CH₂)₃—CONH—CH₂—CH₂-(1-methylpyrrolidin-2-yl) | XVII | (1-methylpyrrolidin-2-yl)methyl | H |
| HOOC—(CH₂)₃—CO—NH—CH₂—CH₂—N(piperidino) | XVIII | piperidinomethyl | H |
| HOOC—(CH₂)₃—CO—NH—CH₂—CH₂—N(pyrrolidino) | XI | pyrrolidinomethyl | H |
| HOOC—(CH₂)₃—CO—NH—CH₂—CH₂-(thien-2-yl) | XX | thien-2-ylmethyl | H |
| HOOC—(CH₂)₃—CO—NH—CH₂—CH₂-(1-methylimidazol-4-yl) | XXI | (1-methylimidazol-4-yl)methyl | H |
| HOOC—(CH₂)₃—CO—NH—CH(COOH)—CH₂-(thien-2-yl) | XXII | thien-2-ylmethyl | H |

The compounds of general formula (I) may be prepared, for example, as described in RU 2005118635 by adding an anhydride of glutaric or succinic acid in a water-immiscible organic solvent to an aqueous solution of amino acid of the general formula:

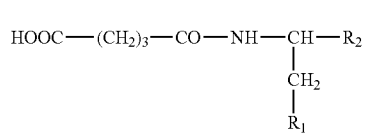

(I)

wherein R₁ is:

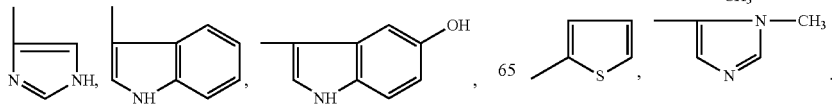

.

This method makes it possible to use an excess of an acylating agent, achieve complete acylation of the α-amino group of amino acid and a yield of the desired product of about 70%. In order to support the necessary pH an organic compound—pyridine, is used, which does not hydrolyze the anhydride, and, furthermore, as is known, is an acylation catalyst. The use of pyridine makes it possible to avoid impurity of the final product with inorganic salts, which together with the reaction product remain in the aqueous layer. The ways that are used make it possible to simplify separation of the desired product from the unreacted anhydride and corresponding amino acid and isolate the desired product by simple crystallization.

The compounds of general formula (I) may also be obtained in the form of pharmaceutically acceptable salts by reaction with, for example, sodium hydroxide, potassium hydroxide, magnesium carbonate, lithium hydroxide, calcium carbonate using routine methods widely described in literature.

The compounds of general formula (I) have anti-arrhythmic activity and may be used for treatment of arrhythmia.

The compounds of general formula (I) are administered in an effective amount, which provides for the desired therapeutic result.

In order to provide treatment of arrhythmia, compounds of general formula I may be administered orally and intravenously in the form of standard dosage forms comprising nontoxic pharmaceutically acceptable carriers.

Compounds of general formula (I) may be administered to a patient in doses that are from 0.01 to 10 mg per kg of body weight daily, preferably in doses from 0.05 to 5 mg/kg once or more times daily.

Wherein, it should be noted that a concrete dose for each concrete patient will depend on many factors, including the activity of the particularly used compound, age, body weight, sex, general health condition and dietary pattern of the patient, the time and method for administration of the medicament, the rate of its removal from the organism, the combination of specifically used medicaments, and also the severity of the disease of this individual undergoing treatment.

The pharmaceutical compositions according to the instant invention comprise a compound of general formula (I) in an amount that is effective for achievement of the desired result, and may be administered in the form of standard dosage forms (for example, in solid, semisolid or liquid forms), comprising compounds of the instant invention as the active ingredient in a mixture with a carrier or excipient that is suitable for parenteral and oral administration. The active ingredient may be introduced into the composition together with usually used nontoxic pharmaceutically acceptable carriers that are suitable for the preparation of solutions, tablets, pills, capsules, dragée and any other dosage forms.

Different substances, such as saccharides, for example, glucose, lactose or saccharose, mannitol or sorbitol, cellulose derivatives and/or calcium phosphates, for example, tribasic calcium phosphate or calcium acid phosphate may be used as the filler. Such substances as starch paste, for example, corn, wheat, rice, potato starch, gelatin, tragacanth, methylcellulose, hydroxypropyl methylcellulose, sodium carboxy methylcellulose and/or polyvinylpyrrolidone may be used as the binder component. If necessary, loosening agents, such as the aforesaid starches and carboxymethyl starch, cross-linked polyvinylpyrrolidone, agar or alginic acid or a salt thereof, such as sodium alginate, may be used.

Optional additives, for example, agents regulating fluidity, and lubricating agents, such as silicon dioxide, talc, stearic acid and salts thereof, such as magnesium stearate or calcium stearate and/or propylene glycol, may be used.

Stabilizers, thickeners, dyes and aromatizers may also be used as additives.

Upon the preparation of a standard dosage form, the amount of the active ingredient that is used in combination with the carrier may vary depending on the recipient subjected to treatment and also on the concrete method of administering the medicament.

So, for example, upon the use of compounds of general formula (I) in the form of solutions for injection, the content of the active agent therein is 0.01-5%. A 0.9% solution of sodium chloride, distilled water, a novocaine solution for injection, a Ringer solution, a glucose solution, and specific additives for dissolution may be used as diluents. Upon the administration into the organism of compounds of the instant invention in the form of tablets, the content thereof is 5.0-500 mg per standard dosage form.

The dosage forms of the instant invention are obtained in accordance with standard methods such as, for example, the processes of mixing, granulating, forming dragees, dissolution and lyophilization.

A study in detail of the pharmacological activity of compounds of general formula (I) is presented in the following examples.

Results of a Study of the Pharmacological Activity
of Compounds of General Formula (I)

EXAMPLE 1

Anti-Arrhythmic Activity of Compounds of General Formula (I) and N-succinyl-D,L-tryptophane dipotassium salt and Also the Effect Thereof on Mortality Upon Adrenal Arrhythmia in Mice Adrenal disorders of cardiac rhythm were reproduced on pedigreeless white laboratory mice of either sex having a weight of 18-22 g. Experimental arrhythmia in the animals was caused in accordance with the method described in the source Moore E. N., Spear J. F. Acute animal models for the study of antiarrhythmic drugs for the prevention of sudden coronary death.//Clin. Pharmacol. Antiarhythmic Therapy. New-York. 1984. pp. 31-46.

The results of comparative testing of the claimed compounds and N-succinyl-D,L-tryptophane dipotassium salt are presented in Table 2.

TABLE 2

Effectiveness of compounds of general formula (I) and N-succinyl-D,L-tryptophane dipotasassium salt upon adrenal intoxication in mice

| No. | Trial conditions, dose (mg/kg) | in trial | with ventricular arrhythmia | with AV blockage | lethal | Life-time (min) |
|---|---|---|---|---|---|---|
| 1 | Control | 14 | 14 (100%) | 14 (100%) | 14 (100%) | 15 ± 2 |
| 2 | Propranolol (0.1) | 14 | 4* (29%) | 5* (36%) | 12 (86%) | 20 ± 4 |
|   | Propranolol (0.5) | 14 | 7* (50%) | 4* (29%) | 11 (79%) | 23 ± 4* |

TABLE 2-continued

Effectiveness of compounds of general formula (I)
and N-succinyl-D,L-tryptophane dipotasassium
salt upon adrenal intoxication in mice

| No. | Trial conditions, dose (mg/kg) | in trial | Number of animals in groups with ventricular arrhythmia | with AV blockage | lethal | Lifetime (min) |
|---|---|---|---|---|---|---|
| 3 | N-succinyl-D,L-tryptophane dipotassium salt (0.05) | 14 | 6* (43%) | 6* (43%) | 14 (100%) | 16 ± 4 |
| 4 | N-succinyl-D,L-tryptophane dipotassium salt (0.5) | 14 | 6* (43%) | 8 (57%) | 14 (100%) | 16 ± 4 |
| 5 | Compound III (0.05) | 14 | 6* (43%) | 4* (29%) | 12 (86%) | 32 ± 7* |
| 6 | Compound III (0.5) | 14 | 4* (29%) | 3* (21%) | 11 (79%) | 33 ± 5* |
| 7 | Compound II mono-sodium salt 0.5 mg/kg | 14 | 0* (0%) | 5* (36%) | 7* (50%) | 19 ± 2.8 |
| 8 | Compound II mono-sodium salt 0.05 mg/kg | 14 | 0* (0%) | 0* (0%) | 7* (50%) | 22 ± 3.4 |
| 9 | Compound IV 0.5 mg/kg | 14 | 2* (14%) | 4* (29%) | 14 (100%) | 18 ± 0.8 |
| 10 | Compound IV 0.05 mg/kg | 14 | 4* (29%) | 3* (21%) | 11 (79%) | 24 ± 3* |
| 11 | Compound II 0.5 mg/kg | 14 | 0* (0%) | 4* (29%) | 7* (50%) | 19 ± 2.8 |
| 12 | Compound II 0.05 mg/kg | 14 | 0* (0%) | 0* (0%) | 7* (50%) | 22 ± 3.4 |
| 13 | Compound XIII mono-sodium salt 0.5 mg/kg | 14 | 3* (21%) | 4* (29%) | 5* (36%) | 28 ± 9* |
| 14 | Compound XIII mono-sodium salt 0.05 mg/kg | 14 | 5* (36%) | 6* (43%) | 6* (43%) | 17 ± 4 |
| 15 | Compound X 0.5 mg/kg | 10 | 3* (30%) | 6 (60%) | 7* (70%) | 27 ± 6* |
| 16 | Compound X 0.05 mg/kg | 10 | 6* (60%) | 7 (70%) | 7* (70%) | 13 ± 4 |
| 17 | Compound IX, 0.5 mg/kg | 10 | 2* (20%) | 5 (50%) | 6* (60%) | 32 ± 4* |
| 18 | Compound IX 0.05 mg/kg | 10 | 7 (70%) | 10 (100%) | 8 (80%) | 21 ± 6 |

*P < 0.05 versus the control group
AV—atrioventricular.

Results of Testing

Compounds of general formula (I), introduced internally in doses of 0.05 and 0.5 mg/kg, had an expressed anti-arrhythmic effect: they prevented the development of blockades for carrying out and episodes of ventricular tachycardia. Wherein, the substances had a number of specificities in the effect on the death [mortality] rate of the test animals. The compound $N^\alpha$-glutaryl-L-histidine (0.05 and 0.5 mg/kg), and also glutaryl histamine (in a dose of 0.05 mg/kg) effectively increased the life span of the test animals, while the compound mono-sodium salt $N^\alpha$-glutaryl-L-tryptophane (0.05 and 0.5 mg/kg) statistically reliably reduced the lethality of the test animals. The low lethality upon the administration of a compound of the mono-sodium salt of $N^\alpha$-glutaryl-L-tryptophane combined with elimination of the ventricular ectopic complexes in all of the test animals.

So, in respect to the degree of anti-arrhythmic action the compounds of general formula (I) exceed that of N-succinyl-D,L-tryptophane dipotassium salt, also administered internally. In contrast to N-succinyl-D,L-tryptophane dipotassium salt, the compounds of general formula (I) reliably increase the life span and reduce the frequency of lethal consequences upon administration internally in the studied doses.

EXAMPLE 2

Activity of Compound III ($N^\alpha$-glutaryl-L-histidine) and of N-succinyl-D,L-tryptophane dipotassium salt on Models of Aconitic Arrhythmia in Mice Arrhythmia was reproduced according to the method of Ju. I. Vikhlyayev and N. V. Kaverina (1958) [Kaverina N. V., Berdyaev S. Ju., Kuschuk E. P., Paskhina O. E. Methodical indications in respect to a study of the anti-arrhythmic activity of new pharmacological substances. Manual on experimental (pre-clinical) study of new pharmacological substances. Edited by V. P. Fisenko.—Moscow. 2000. Page 210]. Aconitine nitrate was administered to the animals in a dose of 50 µg/kg intravenously.

This model makes it possible to assess the scope of the therapeutic action of the presented compounds and the N-succinyl-D.L-tryptophane dipotassium salt. Assessment of the scope of the therapeutic action was carried out in accordance with the value of the anti-arrhythmic index (AAI), determined as the ratio $LD_{50}$ upon the oral method of administering to $ED_{50}$ on an aconitic model of arrhythmia. The results of the calculations are presented in Table 3.

TABLE 3

Effective doses, $LD_{50}$, AAI for the compound III ($N^\alpha$-glutaryl-L-histidine) and N-succinyl-D,L-tryptophane dipotassium salt, calculated in respect to an aconitic model of arrhythmia in mice

| Tested preparation | Method of administration | $ED_{50}$, mg/kg | $LD_{50}$, mg/kg (per/ os mice) | AAI ($LD_{50}$/$ED_{50}$) |
|---|---|---|---|---|
| N-succinyl-D,L-tryptophane potassium salt | per/os | Het* | N.d. | |
| Compound III | per/os | 0.185 ± 0.083 | 4500 | 24324 |

Note:
*$ED_{50}$ was not determined, since in the interval of doses 0.05-5 mg/kg arrhythmia develops in 71-100% of the test animals, while at a dose of 50 mg/kg 50% of the animals died after administration of the substance.

The experiment that was carried out shows that compound III ($N^\alpha$-glutaryl-L-histidine) upon administration internally effectively prevents atrioventricular heart arrhythmia caused by the intravenous administration of aconitine nitrate. Wherein the meaning of $ED_{50}$, calculated for the compound III ($N^\alpha$-glutaryl-L-histidine), shows that the compound III ($N^\alpha$-glutaryl-L-histidine) has a broader scope of therapeutic action than N-succinyl-D,L-tryptophane dipotassium salt, which shows that the former (compound III) is safer upon equivalent activity.

EXAMPLE 3

A Study of the Effect of Compound III ($N^\alpha$-glutaryl-L-histidine) and of N-succinyl-D,L-tryptophane dipotassium salt on the Course of Early Occlusive Arrhythmia in Cats At present, in order to assess the effectiveness of therapy under conditions of transistor ischemic arrhythmogenesis, a method is used that is described by Storozhuk V G. [Antifibrilic activity of some anti-arrhythmic agents upon maximum coronary artery ligation and the reperfusion thereof in cats. Pharmacology and Toxicology. 1985. No. 3, pp. 47-49].

The results of a study of compound III ($N^\alpha$-glutaryl-L-histidine), N-succinyl-D,L-tryptophane dipotassium salt and classical anti-arrhythmics are presented in Table 4.

TABLE 4

Anti-arrhythmic activity of compound III ($N^\alpha$-glutaryl-L-histidine), comparative preparations and N-succinyl-D,L-tryptophane dipotassium salt on models of occlusive arrhythmia in cats

| No. | Studied substance or preparation, dose (mg/kg) | n | Number of animals with ventricular arrhythmia | Time of occurrence of arrhythmia, min | Animals died in group |
|---|---|---|---|---|---|
| 1 | Control | 31 | 23 (74%) | 18 ± 5 | 7 (23%) |
| 2 | Propranolol (1.0) | 7 | 2 (28%)* | 24 ± 1 | 0 |
| 3 | Cordaron (1.0) | 10 | 4 (40%)* | 21 ± 6 | 0 |
| 6 | N-succinyl-D,L-tryptophane dipotassium salt (0.05) | 6 | 3 (50%) | 19 ± 3 | 0 |
| 7 | N-succinyl-D,L-tryptophane dipotassium salt (0.5) | 6 | 1 (17%)* | 21 | 0 |
| 8 | Compound III (0.05) | 8 | 2 (25%)* | 18 ± 2 | 0 |
| 9 | Compound III (0.5) | 6 | 1 (17%)* | 18 | 0 |
| 10 | Compound II (0.05) | 7 | 6 (86%) | 17 ± 2 | 1 (14%) |
| 11 | Compound II (0.5) | 7 | 2 (29%)* | 17-20 | 0 |

Note:
*distinctions from corresponding index in control reliable at p < 0.05.

The compounds were administered intravenously in doses: compound III ($N^\alpha$-glutaryl-L-histidine) and N-succinyl-D,L-tryptophane dipotassium salt—0.05 and 0,5 mg/kg, cordaron and propranolol—1.0 mg/kg.

In the control, ligation of the coronary artery in cats was accompanied by development of ventricular arrhythmia in 74% of the tests. N-succinyl-D,L-tryptophan dipotassium salt did not demonstrate a reliable anti-arrhythmic effect upon administration in a dose of 0.05 mg/kg, while the compound III ($N^\alpha$-glutaryl-L-histidine) upon intravenous administration in the indicated dose had reliable activity. In a dose of 0.5 mg/kg, the compound III ($N^\alpha$-glutaryl-L-histidine) and N-succinyl-D,L-tryptophane dipotassium salt showed similar therapeutic activity.

The presented data show that under conditions of modeling acute occlusive damage to the myocardium in cats, the compound III ($N^\alpha$-glutaryl-L-histidine) upon prophylactic intravenous administration is more effective in a broader range of doses than N-succinyl-D,L-tryptophane dipotassium salt.

The compound III ($N^\alpha$-glutaryl-L-histidine) and N-succinyl-D,L-tryptophane dipotassium salt prevented experimental lethality of the animals in this model, wherein it was 23% in the control.

So, the study of compounds of general formula (I) on different models upon peroral and intravenous administration makes it possible to increase the effectiveness and safety of carrying out anti-arrhythmic therapy. The advantage of the claimed compounds is the large scope of therapeutic action.

Examples of Dosage Forms

A. Tableted Form

A tableted form is obtained, using the ingredients indicated below:

| | |
|---|---|
| Compound corresponding to general formula (I) or a pharmaceutically acceptable salt thereof | 1-150 mg |
| Potato starch | 20-50 mg |
| Magnesium stearate | 3 mg |
| Aerosyl | 1 mg |
| Lactose | to 300 mg |

The components are mixed and pressed to form tablets weighing 300 mg each.

B. Solution for Injections

Example of the makeup of a solution for injection:

| | |
|---|---|
| Compound corresponding to general formula (I) or a pharmaceutically acceptable salt thereof | 0.2-20 mg |
| Water for injection | 2 ml |

The invention claimed is:

1. A method of treating arrhythymia in a mammal in need thereof, comprising administering to the mammal an effective amount of a compound of formula (I):

$$HOOC-(CH_2)_3-CO-NH-CH-R_2 \atop {\phantom{HOOC-(CH_2)_3-CO-NH-}CH_2 \atop \phantom{HOOC-(CH_2)_3-CO-NH-}R_1}$$

wherein $R_1$ =

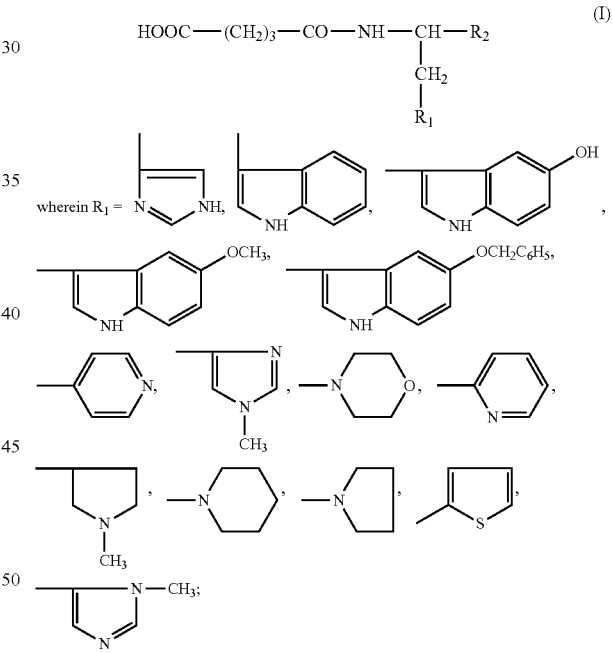

$R_2$ = COOH, —COOCH$_3$, —COOC$_2$H$_5$, H, or a pharmaceutically acceptable salt thereof.